(12) United States Patent
Bolz et al.

(10) Patent No.: US 10,053,440 B2
(45) Date of Patent: Aug. 21, 2018

(54) INTEGRATED PROCESS FOR MAKING PROPENE OXIDE AND AN ALKYL TERT-BUTYL ETHER

(71) Applicants: EVONIK DEGUSSA GMBH, Essen (DE); THYSSENKRUPP INDUSTRIAL SOLUTIONS AG, Essen (DE)

(72) Inventors: David Bolz, Frankfurt (DE); Holger Wiederhold, Darmstadt (DE)

(73) Assignees: EVONIK DEGUSSA GMBH, Essen (DE); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 15/542,923

(22) PCT Filed: Jan. 8, 2016

(86) PCT No.: PCT/EP2016/050269
§ 371 (c)(1),
(2) Date: Jul. 11, 2017

(87) PCT Pub. No.: WO2016/113193
PCT Pub. Date: Jul. 21, 2016

(65) Prior Publication Data
US 2018/0002300 A1    Jan. 4, 2018

(30) Foreign Application Priority Data
Jan. 14, 2015 (EP) ..................... 15151050

(51) Int. Cl.
*C07D 301/02* (2006.01)
*C07D 301/19* (2006.01)
(Continued)

(52) U.S. Cl.
CPC .......... *C07D 301/19* (2013.01); *B01J 21/063* (2013.01); *C01B 15/023* (2013.01); *C07C 5/32* (2013.01); *C07C 41/06* (2013.01); *C07C 43/046* (2013.01)

(58) Field of Classification Search
CPC .... C07D 301/12; C07D 301/32; C07C 5/333; C07C 41/09; C07C 41/34; C01B 15/029
(Continued)

(56) References Cited

U.S. PATENT DOCUMENTS 4,517,395 A  5/1985  Obenaus et al.
5,244,929 A  9/1993  Gottlieb et al.
(Continued)

FOREIGN PATENT DOCUMENTS

EP  0 100 119  2/1984
EP  0 267 556  5/1988
(Continued)

OTHER PUBLICATIONS

International Search Report for PCT/EP2016/050269 filed Jan. 8, 2016.
(Continued)

*Primary Examiner* — Taylor V Oh
(74) *Attorney, Agent, or Firm* — Law Office of: Michael A. Sanzo, LLC (57) ABSTRACT

An integrated process for making propene oxide and an alkyl tert-butyl ether comprises dehydrogenating a feed stream comprising propane and iso-butane to provide a stream comprising propene, iso-butene and hydrogen; separating this stream into a stream consisting essentially of hydrogen and a stream comprising propene and iso-butene; separating the stream comprising propene and iso-butene into a stream comprising propene and a stream comprising iso-butene; reacting a part or all of the stream comprising
(Continued)

iso-butene with an alkanol in the presence of a solid acid catalyst to provide an alkyl tert-butyl ether; and reacting a part or all of the stream comprising propene with hydrogen peroxide in the presence of an epoxidation catalyst to provide propene oxide.

17 Claims, 2 Drawing Sheets

(51) Int. Cl.
    *C07C 41/06*     (2006.01)
    *C07C 43/04*     (2006.01)
    *C07C 5/32*     (2006.01)
    *C01B 15/023*     (2006.01)
    *B01J 21/06*     (2006.01)

(58) Field of Classification Search
    USPC .................................................. 549/510, 518
    See application file for complete search history.

(56) References Cited

U.S. PATENT DOCUMENTS

| | | | |
|---|---|---|---|
| 5,274,140 A | 12/1993 | Venturello et al. | |
| 5,276,212 A * | 1/1994 | Luebke | C07C 41/06 568/697 |
| 5,417,938 A | 5/1995 | Shelden et al. | |
| 5,424,458 A * | 6/1995 | Sullivan | C07C 41/06 549/529 |
| 5,599,956 A | 2/1997 | Pujado et al. | |
| 5,675,045 A | 10/1997 | Bueschken et al. | |
| 5,831,135 A | 11/1998 | Bueschken et al. | |
| 6,337,429 B1 | 1/2002 | Kindler et al. | |
| 6,756,028 B2 | 6/2004 | Korl et al. | |
| 6,861,042 B2 | 3/2005 | Korl et al. | |
| 7,173,143 B2 | 2/2007 | Bender et al. | |
| 2003/0009041 A1 * | 1/2003 | Haas | C07D 301/12 549/531 |
| 2018/0002299 A1 | 1/2018 | Bolz et al. | |

FOREIGN PATENT DOCUMENTS

| | | |
|---|---|---|
| EP | 0 376 117 | 7/1990 |
| EP | 0 428 265 | 5/1991 |
| WO | WO 02/085873 | 10/2002 |
| WO | WO 2004/048355 | 6/2004 |
| WO | WO 2005/000827 | 1/2005 |
| WO | WO 2011/063937 | 6/2011 |
| WO | WO 2013/057120 | 4/2013 |

OTHER PUBLICATIONS

Written Opinion of the International Searching Authority for PCT/EP2016/050269 filed Jan. 8, 2016.
International Preliminary Report on Patentability for PCT/EP2016/050269 filed Jan. 8, 2016.
International Search Report for PCT/EP2016/050246 (international counterpart of co-pending U.S. Appl. No. 15/542,917), filed Jan. 8, 2016.
Written Opinion of the International Searching Authority for PCT/EP2016/050246 (international counterpart of copending U.S. Appl. No. 15/542,917), filed Jan. 8, 2016.
International Preliminary Report on Patentability for PCT/EP2016/050246 (international counterpart of co-pending U.S. Appl. No. 15/542,917), filed Jan. 8, 2016.
Friedlander, et al., "Make plasticizer olefins via n-butene dimerization," Hydrocarbon Process, Int. Ed. (Feb. 1986) 65 (2. Sect. 1), pp. 31-33 as the OCTOL process.
Vernikovskaya, et al., "Dehydrogenation of propene-isobutane reactor over $Cr_2O_3/Al_2O_3$ catalyst: Experimental studies and mathematical modeling," *Chem. Eng. J.* 176-177:158-164 (accepted May 2011).
Office Action for copending U.S. Appl. No. 15/542,917, dated Nov. 14, 2017.
Response to Office Action of Nov. 14, 2017 for copending U.S. Appl. No. 15/542,917, filed Feb. 13, 2018.
U.S. Appl. No. 15/542,917, filed Jul. 11, 2017, US—2018/0002299 A1, Jan. 4, 2018, Bolz.
Notice of Allowance for copending U.S. Appl. No. 15/542,917, dated Apr. 27, 2018.

* cited by examiner

INTEGRATED PROCESS FOR MAKING PROPENE OXIDE AND AN ALKYL TERT-BUTYL ETHER

CROSS REFERENCE TO RELATED APPLICATIONS

The present application is US national stage of international application PCT/EP2016/050269, which had an international filing date of Jan. 8, 2016, and which was published in English under PCT Article 21(2) on Jul. 21, 2016. Priority is claimed to European application EP 15151050.0, filed on Jan. 14, 2015.

FIELD OF THE INVENTION

The present invention is directed to a an integrated process for making propene oxide and an alkyl tert-butyl ether, which makes efficient use of feed materials and process equipment and at the same time allows a variation in the ratio of propene oxide to alkyl tert-butyl ether product over a broad range.

BACKGROUND OF THE INVENTION

A coupled production of propene oxide and methyl tert-butyl ether (MTBE) is known from the prior art using the so called Halcon process, where iso-butane is oxidized with air to tert-butyl hydroperoxide, which is then reacted with propene in the presence of a molybdate catalyst to give propene oxide and tert-butanol. The tert-butanol is further reacted with methanol to give MTBE. However, such a coupled production, where both products are obtained at an essentially fixed ratio, has a disadvantage when market demand for the two products does not match this product ratio. Since the demand for propene oxide has grown more rapidly in recent years than the demand for MTBE, the HPPO process for making propene oxide from propene and hydrogen peroxide has been developed as a stand-alone process for making propene oxide. An integration of the HPPO process with a propane dehydrogenation, where hydrogen obtained in propane dehydrogenation is used as feed for making hydrogen peroxide for the HPPO process, has been proposed in U.S. Pat. No. 5,599,956 and WO 2004/020423.

A dehydrogenation of mixtures of iso-butane and propane using an alumina supported chromium oxide catalyst in a fluidized bed and providing both iso-butene and propene is known from N. V. Vernikovskaya et al., Chem. Eng. J. 167-177 (2011) 158-164.

SUMMARY OF THE INVENTION

The inventors of the present invention have now found a way of integrating the hydrogen peroxide based manufacture of propene oxide with the production of MTBE which can use a mixture of propane and butanes, known as liquefied petroleum gas (LPG), as raw material and is flexible with regard to the production ratio of products propene oxide and MTBE.

Subject of the invention is therefore an integrated process for making propene oxide and an alkyl tert-butyl ether comprising the steps:

a) a step of dehydrogenating a feed stream S1 comprising propane and iso-butane, providing a stream S2 comprising propene, iso-butene and hydrogen;

b) a separation step separating stream S2 into a stream S3 consisting essentially of hydrogen and a stream S4 comprising propene and iso-butene;

c) a separation step separating stream S4 into a stream S5 comprising propene and a stream S6 comprising iso-butene;

d) a step of reacting a part or all of stream S5 with hydrogen peroxide in the presence of an epoxidation catalyst, providing a stream S7 comprising propene oxide;

e) a separation step separating propene oxide from stream S7;

f) a step of reacting a part or all of stream S6 with an alkanol in the presence of a solid acid catalyst, providing a stream S8 comprising an alkyl tert-butyl ether; and g) a separation step separating the alkyl tert-butyl ether from stream S8.

DETAILED DESCRIPTION OF THE INVENTION

In step a) of the integrated process of the invention, a feed stream S1 comprising propane and iso-butane is dehydrogenated to provide a stream S2 comprising propene, iso-butene and hydrogen.

Feed stream S1 may be a liquefied petroleum gas or a low boiling product of a catalytic hydrocracking process. The ratio of propane to butanes in the feed stream may be adjusted as needed for the desired production ratio of products propene oxide and MTBE by separating part of the propane or part of the butanes by distillation.

Preferably, feed stream S1 is provided by the additional steps of separating a feed stream comprising propane and n butane into a stream comprising propane and a stream comprising n-butane, isomerizing n-butane to iso-butane, and combining the iso-butane with a part or all of the stream comprising propane to give feed stream S1.

The feed stream comprising propane and n butane can be separated into a stream comprising propane and a stream comprising n-butane using known methods, such as fractional distillation.

Suitable methods for isomerizing n-butane to iso-butane are known from the prior art and are available for license, such as the Butamer™ process of UOP. In the Butamer™ process, isomerization is preferably carried out at a temperature of 180 to 220° C. and a pressure of 15 to 30 bar by contacting a gas stream containing butane and hydrogen at a molar ratio of from 0.5 to 2 with a platinum catalyst supported on alumina and activated with chloride. The reaction is carried out by passing the gas stream over a catalyst fixed bed. A chlorinated organic compound is preferably added to the gas stream to maintain chloride activation of the catalyst.

The product stream resulting from the isomerization reaction is preferably separated into an n-butane and an iso-butane fraction. Separation of the product stream into an n-butane and an iso-butane fraction can be achieved by distillation. A part or the entire n-butane fraction is recycled to the isomerization reaction and the iso-butane fraction or a mixture of the iso-butane fraction and the non-recycled n-butane fraction is combined with a part or all of the stream comprising propane to give feed stream S1. Adjusting the separation efficiency of the distillative separation of n-butane and iso-butane or varying the ratio of n-butane fraction recycled to isomerization to n-butane fraction passed with stream S1 to step a) allows to adjust the ratio of iso-butane to n-butane in feed stream S1 as needed.

Suitable methods for dehydrogenating a stream comprising propane and iso-butane to provide a stream comprising propene, iso-butene and hydrogen are known from the prior art, such as the Catofin™ process of CB&I Lummus or the Oleflex™ process of UOP. Simultaneous dehydrogenation of propane and iso-butane can be carried out at temperatures of from 500 to 700° C. and pressures of from 0.1 to 3 bar in the presence of a dehydrogenation catalyst. Suitable dehydrogenation catalysts are chromium oxide supported on alumina and activated with an alkali metal, used in the Catofin™ process, and platinum, promoted with tin and alkali metals, supported on alumina, used in the Oleflex™ process. The Catofin™ process is carried out with several adiabatic fixed bed reactors operated in parallel, alternating reactor operation between endothermal dehydrogenation and exothermal catalyst regeneration with air. In the Catofin™ process, dehydrogenation is preferably carried out at 540 to 680° C. and 0.1 to 0.6 bar. The Oleflex™ process is operated with a series of adiabatic moving bed reactors with gas heating between reactors and external catalyst regeneration. In the Oleflex™ process, dehydrogenation is preferably carried out at 550 to 650° C. and 1.0 to 2.6 bar.

In step b) of the integrated process of the invention, stream S2 obtained in step a) is separated into a stream S3 consisting essentially of hydrogen and a stream S4 comprising propene and iso-butene. Stream S2 is preferably cooled and compressed to condense hydrocarbons, providing stream S3 as a gas phase rich in hydrogen. The gas phase can be further purified, preferably by a pressure swing adsorption. Methods for purifying hydrogen by pressure swing adsorption are known from the prior art. The condensed hydrocarbons may be passed as stream S4 to step c). Alternatively, the condensed hydrocarbons are purified by distillation, removing hydrocarbons having less than 3 carbon atoms as an overhead product and hydrocarbons having more than 4 carbon atoms as a bottoms product, to provide a stream S4 consisting essentially of hydrocarbons having 3 or 4 carbon atoms.

In step c) of the integrated process of the invention, stream S4 is separated into a stream S5 comprising propene and a stream S6 comprising iso-butene. The separation can be carried out by known methods and is preferably carried out by fractional distillation.

In a preferred embodiment, unreacted propane is separated from stream S5 and recycled to step a) before stream S5 is passed to step d). The separation of unreacted propane from propene can be carried out by known methods and is preferably carried out by fractional distillation, most preferably in a continuously operated rectification column.

In step d) of the integrated process of the invention, a part or all of stream S5 is reacted with hydrogen peroxide in the presence of an epoxidation catalyst, providing a stream S7 comprising propene oxide. Hydrogen peroxide can be used as an aqueous solution, preferably containing from 20 to 75% by weight hydrogen peroxide and most preferably from 40 to 70% by weight. Both homogeneous and heterogeneous epoxidation catalysts may be used in step d). Suitable epoxidation catalysts and reaction conditions for reacting stream S5 with hydrogen peroxide to form propene oxide are known from the prior art. Suitable homogeneous epoxidation catalysts are manganese complexes with polydentate nitrogen ligands, in particular 1,4,7 trimethyl-1,4,7-triazacyclononane ligands, as known from WO 2011/063937. Other suitable homogeneous epoxidation catalysts are heteropolytungstates and heteropolymolybdates, in particular polytungstophosphates, as known from U.S. Pat. No. 5,274,140. Suitable heterogeneous epoxidation catalysts are titanium zeolites containing titanium atoms on silicon lattice positions.

Preferably, a titanium silicalite catalyst is used, preferably with an MFI or MEL crystal structure, and most preferably titanium silicalite 1 with MFI structure as known from EP 0 100 119 A1, is used. The titanium silicalite catalyst is preferably employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation, silica being preferred as binder. Extrudates with a diameter of 1 to 5 mm are preferably used as fixed bed catalysts. Epoxidation with a titanium silicalite catalyst is preferably carried out in a methanol solvent. The methanol solvent can be a technical grade methanol, a solvent stream recovered in the work-up of the epoxidation reaction mixture or a mixture of both. The epoxidation is preferably carried out at a temperature of 30 to 80° C., more preferably at 40 to 60° C., and a pressure of from 0.5 to 5 MPa, more preferably 1.5 to 3.5 MPa. The epoxidation is preferably carried out in a fixed bed reactor by passing a mixture comprising propene, hydrogen peroxide and methanol over the catalyst fixed bed. The fixed bed reactor is preferably equipped with cooling means and cooled with a liquid cooling medium. The temperature profile within this reactor is preferably maintained such that the cooling medium temperature of the cooling means is at least 40° C. and the maximum temperature within the catalyst bed is 60° C. at the most, preferably 55° C. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 h−1, preferably 1.3 to 15 h−1. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. Propene is preferably employed in excess relative to the hydrogen peroxide in order to achieve high hydrogen peroxide conversion, the molar ratio of propene to hydrogen peroxide preferably being chosen in the range from 1.1 to 30. The methanol solvent is preferably used in the epoxidation in a weight ratio of 0.5 to 20 relative to the amount of hydrogen peroxide. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions. Most preferably, the epoxidation reaction is carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827.

In step e) of the integrated process of the invention, propene oxide is separated from stream S7 provided in step d) as reaction product. Propene oxide may be separated from stream S7 by distillation or extractive distillation using methods known from the prior art. Preferably, propene oxide is separated from stream S7 by distillation after a pressure release stage which removes most of the non-reacted propene from stream S7. When a methanol solvent is used in step d) and stream S7 comprises methanol, the distillation is preferably carried out in at least two columns, operating the first column to provide a crude propene overhead product containing from 20 to 60% of the methanol contained in stream S7 and further purifying the overhead product by at least one additional distillation. The overhead product is preferably further purified by distilling off remaining propene and propane, followed by extractive distillation, most preferably using the extractive distillation method of WO 2004/048355 for additional removal of carbonyl compounds.

In step f) of the integrated process of the invention, a part or all of stream S6 obtained in step c) is reacted with an alkanol in the presence of a solid acid catalyst to provide a stream S8 comprising an alkyl tert-butyl ether. The alkanol is preferably methanol to provide methyl tert-butyl ether (MTBE) or ethanol to provide ethyl tert-butyl ether (ETBE) and is most preferably methanol.

The solid acid catalyst is preferably an acidic ion exchange resin, more preferably a resin having sulphonic acid groups. Suitable ion exchange resins are sulphonated phenol/aldehyde condensates and cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. Preferably, the acidic ion exchange resin is a sulphonated copolymer of styrene and divinylbenzene. The resin may be a gel resin or a macroporous resin. Suitable ion exchange resins are commercially available under the trade names Duolite® C20 and C26, Amberlyst® 15 and 35, Amberlite® IR 120 and 200, Dowex® 50 and Lewatit® SPC 118 SPC 108, K2611, K2621 and OC 1501, Amberlyst® 15, Amberlyst® 35 and Lewatit® K2621 being preferred. The pore volume of the ion exchange resins is preferably from 0.3 to 0.9 ml/g, especially from 0.5 to 0.9 ml/g. The particle size of the resins is preferably from 0.3 mm to 1.5 mm, especially from 0.5 mm to 1.0 mm.

The reaction is preferably carried out in a fixed bed reactor. When the alkanol is methanol, the reaction is most preferably carried out in two stages, using a liquid-filled fixed bed reactor in the first stage and a reactive distillation column in the second stage.

In the first stage, stream S6 is preferably reacted with methanol at a temperature of 20 to 110° C., more preferably 25 to 70° C., and a pressure of 0.5 to 5 MPa, more preferably 0.7 to 2 MPa, and temperature and pressure are selected to maintain a liquid reaction mixture. The molar ratio of methanol to iso-butene in stream S6 is preferably from 10:1 to 1:1, more preferably from 5:1 to 1.1:1 and most preferably from 1.8:1 to 1.2:1. The first stage is most preferably carried out with two or three fixed bed reactors in series, operating the first reactor at 35 to 70° C. and the second and optionally third reactor at 25 to 50° C. The residence time in the first stage is chosen to provide a composition close to the chemical equilibrium between methanol, iso-butene and MTBE, preferably achieving an isobutene conversion of more than 94%, more preferably more than 96%. Tube bundle reactors and adiabatic fixed bed reactors may be used in the first stage.

In the second stage, the reaction mixture formed in the first stage is further reacted in a reactive distillation column, comprising an acidic ion exchange resin arranged in a reaction zone, operated at a pressure of from 0.5 to 1.5 MPa, preferably 0.75 to 1.0 MPa, and a temperature in the reaction zone of from 50° C. to 90° C., preferably from 55° C. to 70° C., at a reflux ratio between 0.5 and 1.5, preferably between 0.7 and 0.9. The reflux ratio refers to the ratio of the distillate stream returned to the column to the distillate stream removed. The reactive distillation column preferably has separation zones above and below the reaction zone. The separation zone above the reaction zone preferably has from 5 to 20 theoretical plates, in particular from 10 to 15 theoretical plates. The separation zone below the reaction zone preferably has from 12 to 36 theoretical plates, in particular from 20 to 30 theoretical plates. The reaction mixture formed in the first stage is preferably fed to the reactive distillation column below the reaction zone, preferably 3 to 13 and more preferably 4 to 10 theoretical plates below the reaction zone. In the reaction zone, the ion exchange resin may be integrated in a structured packing, for example in KataMax® packings known from EP 0 428 265, KataPak® packings known from EP 0 396 650 or Multi-Pak® packings. Alternatively, it may be polymerized onto shaped bodies as described in U.S. Pat. No. 5,244,929. Preference is given to using KataMax® packings. The amount of ion exchange resin is preferably selected to achieve an isobutene conversion of 75 to 99%, preferably of 85 to 98% and more preferably of 95 to 97%, based on the isobutene content in the feed to the reactive distillation column.

In step g) of the integrated process of the invention, the alkyl tert-butyl ether is separated from stream S8 provided in step f) as reaction product. The alkyl tert-butyl ether is preferably separated from stream S8 by distillation. When the alkanol is methanol and step f) is carried out in two stages as described above, step g) may be integrated with step f) in that the reaction mixture obtained from the first stage and from the reaction zone of the reactive distillation column is separated in the separation zone below the reaction zone to provide MTBE as the bottoms product of the reactive distillation column and in the separation zone above the reaction zone to provide a mixture of methanol and C4 hydrocarbons as the overhead product of the reactive distillation column.

In a preferred embodiment of step g), a stream S10 comprising iso-butane is additionally separated and from this stream S10 a stream S11 comprising more than 80% by weight iso-butane is separated and recycled to step a). The separation of streams S10 and S11 may be carried out by methods known from the prior art, such as distillation, extractive distillation or extraction. When the alkanol is methanol and step f) is carried out in two stages as described above, stream S10 is obtained as the overhead product of the reactive distillation column. Methanol is preferably separated from this overhead product by extracting with an aqueous solution in a liquid-liquid-extraction. The aqueous solution preferably has a pH of at least 8, most preferably 8 to 12. The pH may be adjusted by adding a base, preferably sodium hydroxide. The extraction may be carried out in mixers and settlers or in an extraction column and is preferably carried out in an extraction column operated in counter current. The extraction column has preferably 2 to 25 and more preferably 5 to 15 theoretical plates and is preferably operated at a temperature of 10 to 90° C. and a pressure sufficient to maintain C4 hydrocarbons as a liquid phase. The mass ratio of aqueous solution to the overhead product of the reactive distillation column is preferably from 1:5 to 1:40. If a feed stream S1 consisting essentially of propane and iso-butane is used in step a), extraction of methanol from stream 10 as described above will provide a stream S11 comprising more than 80% by weight iso-butane which can be recycled to step a), optionally with further purification, such as drying.

If only a part of stream S6 obtained in step c) is reacted with an alkanol in step f), the remainder of stream S6 can be used as a feed for a different reaction. Preferably, a feed stream S1 consisting essentially of propane and iso-butane is used in step a) and the part of stream S6 that is not fed to step f) is used as feed for a catalytic partial oxidation converting iso-butene to methacrylic acid. Oxidation of iso-butene to methacrylic acid is preferably carried out in two gas phase oxidation stages via methacrolein as an intermediate. In the first stage, iso-butene is preferably reacted with oxygen at a temperature of from 300 to 420° C. and a pressure of from 1 to 5 bar in the presence of a molybdenum bismuth mixed oxide catalyst which can be promoted with at least one of iron, cobalt, nickel, antimony, tungsten and alkali metals. Preferably, a catalyst having a composition as described in EP 267 556, page 3, lines 19 to 33 is used. The reaction is preferably carried out by passing a gas stream comprising iso-butene, oxygen, water and an inert gas with a volume ratio of iso-butene:$O_2$:$H_2O$:inert gas of 1:0.5-5:1-20:3-30, preferably 1:1-3:2-10:7-20, over a catalyst fixed bed. The inert gas is preferably nitrogen, carbon dioxide, methane or a mixture of nitrogen and carbon dioxide. In the second stage, methacrolein is preferably reacted with oxygen at a temperature of from 250 to 350° C. and a pressure of from 1 to 3 bar in the presence of a phosphomolybdic acid catalyst promoted with an alkali metal, which can be further promoted with at least one of copper, vanadium, arsenic and antimony. Preferably, a catalyst having a composition as described in EP 376 117, page 2, line 50 to page 3, line 21 is used. The catalyst is preferably employed as a fixed bed. The reaction is preferably carried out by passing a gas stream comprising methacrolein, oxygen, water and an inert gas with a volume ratio of iso-butene:$O_2$:$H_2O$:inert gas of 1:1-5:2 20:3-30, preferably 1:1-4:3-10:7-18, over a catalyst fixed bed. In a preferred embodiment, the reaction product stream from the first stage is fed directly as feed to the second stage, optionally with adding further oxygen and/or inert gas. Methacrylic acid and methacrolein are separated from the reaction product gas of the second stage, preferably by condensation, absorption or a combination of both, and the separated methacrolein is preferably returned to the entry of the second stage. Residual gas remaining after separation of methacrylic acid and methacrolein may be subjected to combustion and the combustion gas may be returned to the entry of the first or second stage to provide all or part of the inert gas.

In one embodiment of the integrated process of the invention, feed stream S1 to step a) comprises n-butane. The dehydrogenation of n-butane in step a) will then generate 1-butene, cis-2-butene, trans-2-butene and 1,3-butadiene and stream S6 will comprise these compounds in addition to iso-butene. 1,3-butadiene is preferably removed from stream S6 before reacting stream S6 in step f). 1,3 butadiene can be removed from stream S6 by selective extraction, preferably using N-methylpyrrolidone, most preferably as described in U.S. Pat. No. 6,337,429. Alternatively, 1,3-butadiene can be removed from stream S6 by partial hydrogenation, preferably using the method of DE 31 43 647 and the reactor configuration of DE 195 24 971. In a further preferred embodiment, a stream S10 comprising 1-butene is separated in step g) and from this stream S10 a stream S12 consisting essentially of 1-butene is separated. Stream S10 preferably consists essentially of C4 hydrocarbons and can be obtained from stream S8 by separating the alkyl tert-butyl ether and non-reacted alkanol by known methods, such as distillation, extractive distillation or extraction, as described further above. Stream S10 can be separated in a first rectification step into an overhead product consisting essentially of 1 butene, iso-butene and lower boiling hydrocarbons and a bottoms product, containing essentially all n-butane, cis-2-butene and trans-2-butene fed with stream S10. The first rectification step can be carried out in a rectification column having more than 100 and preferably 150 to 200 theoretical plates, operated at a pressure of 0.4 to 1.0 MPa, preferably 0.5 to 0.7 MPa and a temperature of from 35 to 80° C., preferably 40 to 65° C. The overhead product from the first rectification step can be separated in a second rectification step into a an overhead product containing isobutene and lower boiling hydrocarbons, which can be recycled as stream S11 to step a), and a bottoms product consisting essentially of 1-butene as stream S12. The second rectification step can be carried out in a rectification column having more than 100 and preferably 150 to 200 theoretical plates, operated at a reflux ratio of from 30 to 60. Stream S12 can be used as a comonomer in the preparation of polyethylene (LLDPE or HDPE) and ethylene-propylene copolymers or starting material for the preparation of 2 butanol, butene oxide or valeraldehyde. The bottoms product from the first rectification step can be used as feed for an olefin oligomerization to prepare olefins having eight, twelve, sixteen, twenty or more carbon atoms, which have use as starting materials for making C9 and C13 alcohols for the manufacture of plasticisers, C13, C17 and C21 alcohols for the manufacture of detergents and high purity C16+ paraffins. A suitable methods for olefin oligomerization is known from Hydrocarbon Process, Int. Ed. (1986) 65 (2. Sect.1), pages 31-33 as the OCTOL process.

In a preferred embodiment of the integrated process of the invention, a part or all of stream S3 consisting essentially of hydrogen is reacted with oxygen to give hydrogen peroxide and a part or all of this hydrogen peroxide is fed to step d).

Stream S3 can be reacted with oxygen in a liquid reaction medium in the presence of a noble metal catalyst in what is known as a hydrogen peroxide direct synthesis. The noble metal catalyst is preferably a supported catalyst, with alumina, silica, titanium dioxide, zirconium dioxide, zeolites and activated carbons being preferred supports. The noble metal catalyst may be a suspended catalyst or preferably a fixed bed catalyst. The noble metal catalyst preferably comprises palladium as noble metal, optionally in combination with platinum, gold or silver, a combination of palladium with platinum at a weight ratio of Pd:Pt of more than 4 being most preferred. Oxygen can be used as pure oxygen, air or air enriched in oxygen. Direct synthesis is preferably carried out with a gas composition that is not flammable. For this purpose, an inert gas such as nitrogen or carbon dioxide can be added. Direct synthesis is preferably carried out with a gas mixture containing at most 6% by volume hydrogen and most preferably from 3 to 5% by volume hydrogen. The gas mixture preferably contains preferably from 10 to 50% by volume oxygen and most preferably from 15 to 45% by volume oxygen. Stream S3 and oxygen are preferably dispersed separately in the liquid reaction medium and inert gas can be added either to stream S3 or to the oxygen feed. The liquid reaction medium may be an aqueous, aqueous-organic or organic reaction medium and preferably consists essentially of an alcohol or a mixture of an alcohol and water, the alcohol most preferably being methanol. The liquid reaction medium preferably comprises a halide, more preferably iodide or bromide and most preferably bromide in an amount of $10^{-6}$ to $10^{-2}$ mol/l, preferably $10^{-5}$ to $10^{-3}$ mol/l and most preferably $10^{-5}$ to $5 \cdot 10^{-4}$ mol/l in order to suppress decomposition of hydrogen peroxide on the noble metal catalyst. The liquid reaction medium preferably further comprises a strong acid having a $pK_a$ of less than 3 in an amount of 0.0001 to 0.5 mol/l and preferably 0.001 bis 0.1 mol/l in order to improve selectivity for hydrogen peroxide formation, with sulfuric acid, phosphoric acid, nitric acid and methane sulfonic acid being preferred. The hydrogen peroxide direct synthesis is preferably carried out in a fixed bed reactor operated as bubble column with stream S3, oxygen and optionally inert gas being dispersed below a catalyst fixed bed.

In a preferred embodiment, stream S3 is reacted with oxygen in an anthraquinone process, providing a 20 to 75% by weight aqueous solution of hydrogen peroxide. The anthraquinone process uses a working solution comprising at least one 2-alkylanthraquinone, 2-alkyltetrahydroanthraquinone or a mixture of both, referred to as quinones in the following, and at least one solvent for dissolving the quinone and the hydroquinone. The 2-alkylanthraquinone is preferably 2-ethylanthraquinone (EAQ), 2-amylanthraquinone (AAQ) or 2-(4-methylpentyl)-anthraquinone IHAQ and more preferably a mixture of EAQ with AAQ and/or IHAQ where the molar fraction of quinones carrying an ethyl group is from 0.05 to 0.95. The working solution preferably further comprises the corresponding 2-alkyltetrahydroanthraquinones and the ratio of 2-alkyltetrahydroanthraquinones plus 2-alkyltetrahydroanthrahydroquinones to 2-alkylanthraquinones plus 2-alkylanthrahydroquinones is preferably maintained in the range of from 1 to 20 by adjusting the conditions of the hydrogenating and regenerating steps used in the anthraquinone process. The working solution preferably comprises a mixture of alkylbenzenes having 9 or 10 carbon atoms as solvent for anthraquinones and at least one polar solvent selected from diisobutylcarbinol (DiBC), methylcyclohexylacetate (MCA), trioctylphosphate (TOP), tetrabutylurea (TBU) and N-octylcaprolactam as solvent for anthrahydroquinones, DiBC, MCA and TOP being preferred and TOP being most preferred.

The anthraquinone process is a cyclic process, comprising a hydrogenation stage, where stream S3 is reacted with working solution in the presence of a hydrogenation catalyst to convert at least part of the quinone to the corresponding hydroquinone, a subsequent oxidation stage, where the hydrogenated working solution containing hydroquinone is reacted with oxygen to form hydrogen peroxide and quinone, and an extraction stage, where hydrogen peroxide is extracted from the oxidized working solution with water to provide stream S6 as an aqueous solution of hydrogen peroxide, with the extracted working solution being returned to the hydrogenation stage to complete a reaction cycle.

In the hydrogenation stage, the working solution is reacted with stream S3 in the presence of a heterogeneous hydrogenation catalyst. During the reaction all or a part of the quinones are converted to the corresponding hydroquinones. All hydrogenation catalysts known from the prior art for the anthraquinone cyclic process can be used as catalysts in the hydrogenation stage. Noble metal catalysts containing palladium as the principal component are preferred. The catalysts can be used as a fixed bed catalysts or as a suspended catalyst and suspended catalysts can be either unsupported catalysts, such as palladium black, or supported catalysts, with suspended supported catalysts being preferred. $SiO_2$, $TiO_2$, $Al_2O_3$ and mixed oxides thereof, as well as zeolites, $BaSO_4$ or polysiloxanes, are can be used as support materials for fixed-bed catalysts or supported suspended catalysts, with $TiO_2$ and $SiO_2/TiO_2$ mixed oxides being preferred. Catalysts in the form of monolithic or honeycombed moldings, the surface of which is coated with the noble metal, can also be used. Hydrogenation can be carried out in stirred-tank reactors, tube reactors, fixed-bed reactors, loop reactors or air-lift reactors which can be equipped with devices for distributing stream S3 in the working solution, such as static mixers or injection nozzles. Preferably, a tube reactor with a recycle and a Venturi nozzle for injecting stream S3 into the reactor feed as known from WO 02/34668 is used. Hydrogenation is carried out at a temperature of from 20 to 100° C., preferably 45 to 75° C., and a pressure of from 0.1 MPa to 1 MPa, preferably 0.2 MPa to 0.5 MPa. The hydrogenation is preferably performed in such a way that essentially all hydrogen introduced with stream S3 into the hydrogenation reactor is consumed in a single pass through the reactor. The ratio between stream S3 and working solution fed to the hydrogenation reactor is preferably chosen to convert between 30 and 80% of the quinones to the corresponding hydroquinones. If a mixture of 2-alkylanthraquinones and 2-alkyltetrahydroanthraquinones is used, the ratio between stream S3 and working solution is preferably chosen so that only the 2-alkyltetrahydroanthraquinones are converted to hydroquinones and the 2-alkylanthraquinones remain in the quinone form.

In the oxidation stage, the hydrogenated working solution from is reacted with an oxygen-containing gas, preferably with air or with oxygen enriched air. All oxidation reactors known from the prior art for the anthraquinone process can be used for the oxidation, bubble columns operated in co-current being preferred. The bubble column can be free from internal devices, but preferably contains distribution devices in the form of packings or sieve plates, most preferably sieve plates in combination with internal coolers. Oxidation is carried out at a temperature of from 30 to 70° C., preferably from 40 to 60° C. Oxidation is preferably performed with an excess of oxygen to convert more than 90%, preferably more than 95%, of the hydroquinones to the quinone form.

In the extraction stage, the oxidized working solution containing dissolved hydrogen peroxide is extracted with an aqueous solution to provide an aqueous hydrogen peroxide solution and an extracted oxidized working solution containing essentially no hydrogen peroxide. Deionized water, which may optionally contain additives for stabilizing hydrogen peroxide, adjusting the pH and/or corrosion protection, is preferably used for extracting the hydrogen peroxide. Extraction is preferably carried out in a countercurrent continuous extraction column, sieve-plate columns being most preferred. The aqueous hydrogen peroxide solution obtained by extraction may be fed directly to step d) or may be concentrated by distilling off water at reduced pressure before feeding it to step d). The aqueous hydrogen peroxide solution obtained by extraction may also be purified, preferably by washing with a solvent, which is preferably a solvent comprised in the working solution.

The anthraquinone process preferably comprises at least one additional stage for regenerating the working solution, where by-products formed in the process are converted back to quinones. Regeneration is carried out by treating hydrogenated working solution with alumina or sodium hydroxide, preferably using a side stream to the cyclic process. In addition to regeneration of hydrogenated working solution, extracted oxidized working solution may be regenerated in a side stream using alumina, sodium hydroxide or an organic amine. Suitable methods for regenerating the working solution on an anthraquinone process are known from the prior art.

Figure 1:
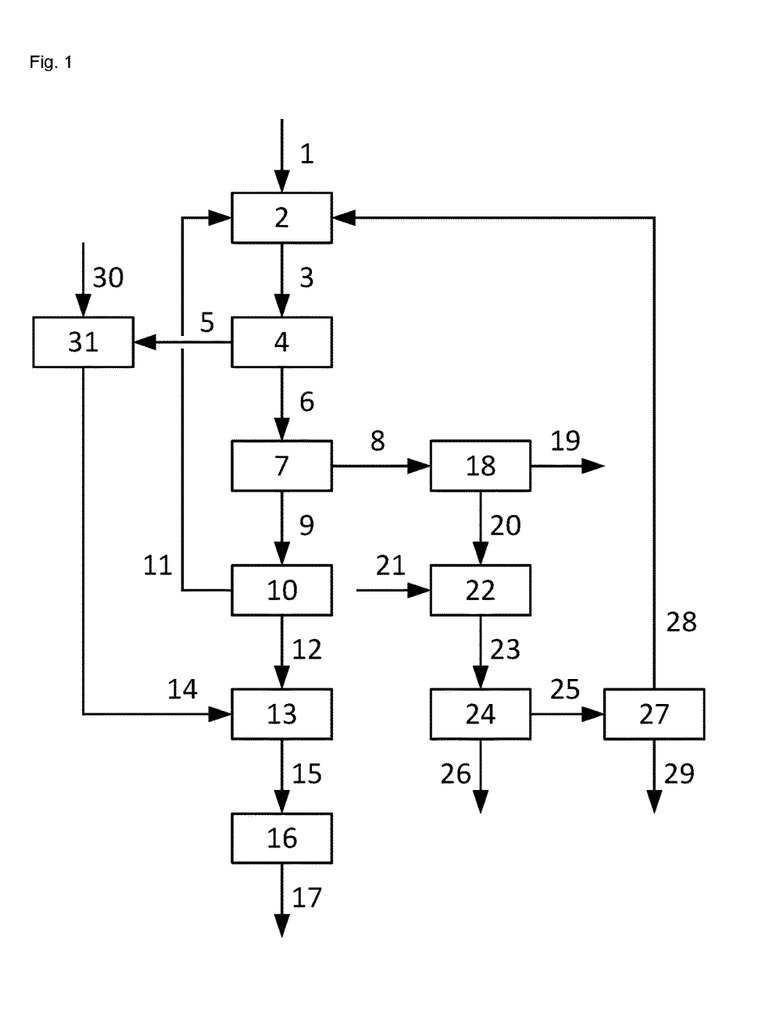
FIG. 1 shows a flow chart for an embodiment of the integrated process where the feed stream to step a) comprises n-butane and a stream consisting essentially of 1-butene is obtained as an additional product.

FIG. 1 shows a flow chart for an embodiment of the integrated process of the invention where a feed stream S1 (1) comprising n-butane in addition to iso-butane and propane is fed to the dehydrogenating step (2) and where hydrogen obtained in the dehydrogenating step is used for making the hydrogen peroxide needed for the epoxidation of propene. Dehydrogenation provides a stream S2 (3) comprising propene, iso-butene and hydrogen. Due to the presence of n butane in stream S1, stream S2 also comprises the linear butenes 1-butene, cis-2-butene and trans-2-butene. Stream S2 also comprises unreacted propane, iso-butane and n butane. Stream S2 (3) is separated in a separation step (4) into a stream S3 (5) consisting essentially of hydrogen and a stream S4 (6) comprising propene and iso-butene. In addition to propene and iso-butene, stream S4 also comprises the linear butenes and unreacted propane, iso-butane and n-butane. Stream S3 (5) is reacted with oxygen (30) in step (31) to give hydrogen peroxide (14). Step (31) is preferably an anthraquinone process using air as oxygen source providing hydrogen peroxide as an aqueous solution. Stream S4 is separated in a separation step (7) into a stream S5 (9) comprising propene and a stream S6 (8) comprising iso-butene. Stream S5 comprises unreacted propane in addition to propene. Stream S6 comprises unreacted iso-butane and n-butane as well as linear butenes in addition to iso-butene. In a further separation step (10), unreacted propane is separated from stream S5 (9) and recycled as stream S9 (11) to the dehydrogenating step (2), providing a stream (12) comprising propene depleted in unreacted propane, which is reacted with hydrogen peroxide (14) in step (13) to provide a stream S7 (15) comprising propene oxide. Step (13) is preferably carried out with a titanium silicalite fixed catalyst in a methanol solvent using a fixed bed reactor. In a subsequent separation step (16), propene oxide (17) is separated from Stream S7 (15). Stream S6 (8) is passed to a step (18) of removing 1,3-butadiene (19) to provide a stream (20) depleted in 1,3-butadiene, comprising iso-butene, n-butenes, iso-butane and n-butane, which is reacted with an alkanol (21) in step (22) in the presence of a solid acid catalyst, providing a stream S8 (23) comprising an alkyl tert-butyl ether. The alkanol is preferably methanol, providing a stream S8 (23) comprising methyl tert-butyl ether. In a subsequent separation step (24), the alkyl tert-butyl ether (26) is separated from stream S8 (23) and a stream S10 (25) comprising unreacted iso-butane and alkanol is obtained. In addition to unreacted iso-butane, stream S10 also contains unreacted n butane and the linear butenes. In a further separation step (27), stream S10 (25) is further separated into a stream S11 (28) comprising more than 80% by weight iso-butane, which is recycled to the dehydrogenating step (2), a stream stream S12 (29) consisting essentially of 1-butene, and one or more streams, not shown in FIG. 1, which comprise alkanol, n-butane, cis-2-butene and trans-2 butene.

Figure 2:
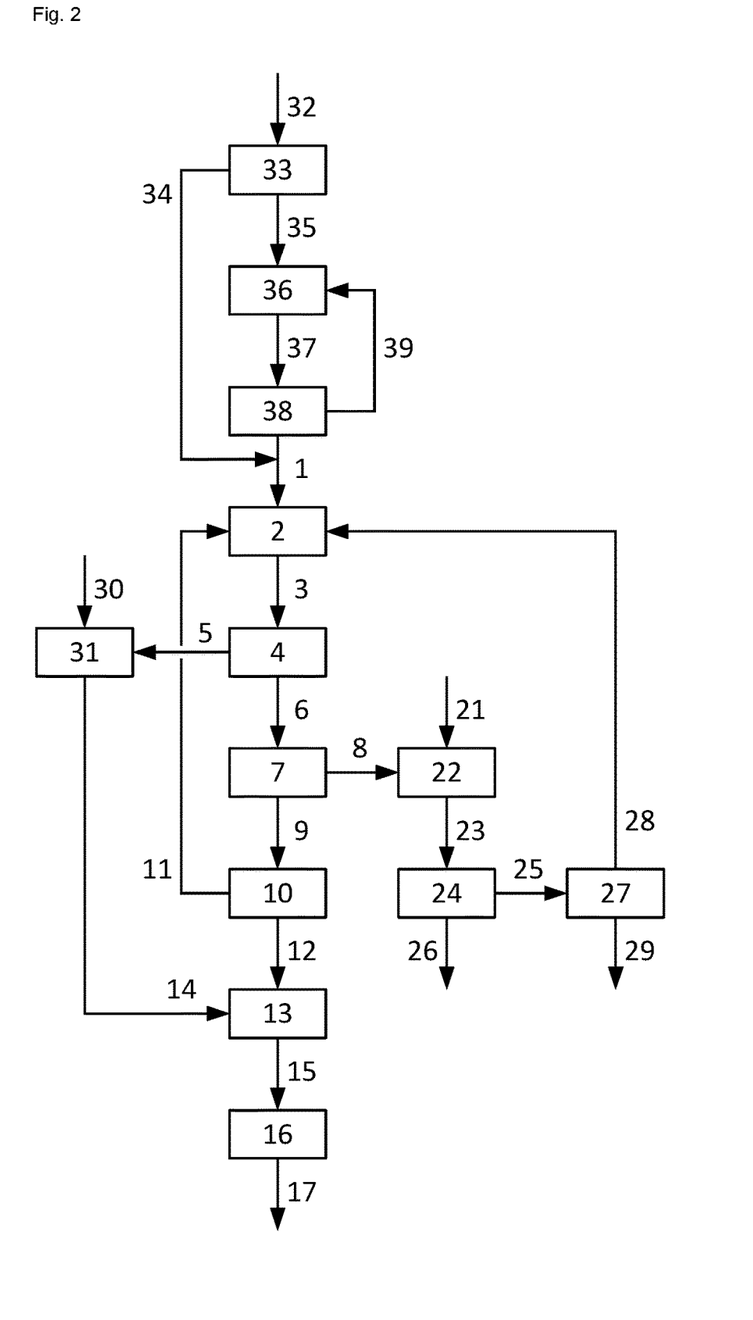
FIG. 2 shows a flow chart for an embodiment of the integrated process additionally comprising a step of separating propane and n butane, a step of isomerizing the separated n-butane to iso-butane, and combining the resulting iso-butane with the separated propane to provide the feed stream to step a).

FIG. 2 shows a flow chart for an embodiment of the integrated process of the invention additionally comprising a step of separating propane and n butane, a step of isomerizing the separated n-butane to iso-butane, and combining the resulting iso-butane with the separated propane to provide the feed stream to step a). separating a A feed stream (32) comprising propane and n butane is separated in step (33) into a stream S13 (34) comprising propane and a stream S14 (35) comprising n-butane. Stream S14 is fed to a step (36) of isomerizing n-butane to iso-butane to provide a stream S15 (37) comprising n-butane and iso-butane, preferably at the equilibrium ratio established at the temperature used in step (36). In a subsequent separation step (38), n-butane is separated from stream S15 (37) and recycled to step (36) of isomerizing n-butane to iso-butane. The resulting iso-butane depleted in n-butane is then combined with stream S13 to give feed stream S1 (1) to the dehydrogenating step (2). In this embodiment, n butane is preferably separated as complete as possible in step (38) in order to provide streams S6 (8), S8 (23) and S10 (25) that contain essentially no n-butane and no linear butenes.

The integrated process of the invention provides an alkyl tert-butyl ether and propene oxide from a mixture of propane and butanes, known as liquefied petroleum gas (LPG), as raw material.

Compared to the Halcon process of coupled production of MTBE and propene oxide, the integrated process of the invention has the advantage of providing high flexibility in varying the production ratio of tert-butyl ether and propene oxide simply by adjusting the ratio of propane to iso-butane in the feed which can be easily achieved by separating propane or butanes from LPG by distillation. The integrated process of the invention uses a dehydrogenation step for simultaneously dehydrogenating propane and butanes which saves on investment costs and makes efficient use of all components present in LPG. The simultaneous dehydrogenation of propane and butanes provides sufficient hydrogen for producing all the hydrogen peroxide needed for epoxidizing propene and nay provide hydrogen for further processes, such as the hydroisomerization of n-butane to iso-butane. If a feed stream comprising n-butane in addition to iso-butane is used, the integrated process of the invention also provides 1-butene as a valuable product. In the embodiment comprising a step of isomerizing n-butane to iso-butane, the production ratios of tert-butyl ether, 1 butene and propene oxide can be varied even more flexibly by varying the ratio of iso-butane to n-butane in feed stream S1.

LIST OF REFERENCE SIGNS

1 Feed stream S1 comprising propane and iso-butane
2 Step of dehydrogenating propane and iso-butane
3 Stream S2 comprising propene, iso-butene and hy-drogen
4 Step of separating hydrogen from propene and iso-butene
5 Stream S3 consisting essentially of hydrogen
6 Stream S4 comprising propene and iso-butene
7 Step of separating propene and iso-butene
8 Stream S6 comprising iso-butene
9 Stream S5 comprising propene
10 Step of separating unreacted propane from stream S5
11 Stream S9 comprising unreacted propane
12 Stream S5 depleted in propane 13 Step of reacting hydrogen peroxide with propene to provide propene oxide
14 Hydrogen peroxide
15 Stream S7 comprising propene oxide
16 Step of separating propene oxide
17 Propene oxide
18 Step of removing 1,3-butadiene from stream S6
19 1,3-Butadiene
20 Stream S6 depleted in 1,3-Butadiene
21 Alkanol
22 Step of reacting iso-butene with alkanol
23 Stream S8 comprising alkyl tert-butyl ether
24 Step of separating alkyl tert-butyl ether
25 Stream S10 comprising unreacted iso-butane
26 Alkyl tert-butyl ether
27 Step of separating unreacted iso-butane
28 Stream S11 comprising more than 80% by weight iso-butane
29 Stream S12 consisting essentially of 1-butene
30 Oxygen
31 Step of reacting hydrogen with oxygen to provide hydrogen peroxide
32 Feed stream comprising propane and n butane
33 Step of separating propane and n butane
34 Stream S13 comprising propane
35 Stream S14 comprising n-butane
36 Step of isomerizing n-butane to iso-butane
37 Stream S15 comprising n-butane and iso-butane
38 Step of separating n-butane and iso-butane
39 Recycle stream S16 comprising n-butane

The invention claimed is:

1. An integrated process for making propene oxide and an alkyl tert-butyl ether comprising;
   a) a step of dehydrogenating a feed stream, S1, comprising propane and iso-butane, to provide a stream, S2, comprising propene, iso-butene and hydrogen;
   b) a separation step separating stream S2 into a stream, S3, consisting essentially of hydrogen and a stream, S4, comprising propene and iso-butene;
   c) a separation step separating stream S4 into a stream, S5, comprising propene and a stream, S6, comprising iso-butene;
   d) a step of reacting a part or all of stream S5 with hydrogen peroxide in the presence of an epoxidation catalyst to provide a stream, S7, comprising propene oxide;
   e) a separation step separating propene oxide from stream S7;
   f) a step of reacting a part or all of stream S6 with an alkanol in the presence of a solid acid catalyst, to provide a stream, S8, comprising an alkyl tert-butyl ether; and
   g) a separation step separating the alkyl tert-butyl ether from stream S8.

2. The process of claim 1, wherein the alkanol is methanol.

3. The process of claim 1, wherein unreacted propane is separated from stream S5 and recycled as a stream, S9, to step a) before stream S5 is reacted in step d).

4. The process of claim 1, wherein a stream, S10, comprising unreacted iso-butane is separated in step g), a stream, S11, comprising more than 80% by weight iso-butane is separated from said stream S10 and said stream S11 is recycled to step a).

5. The process of claim 1, wherein the feed stream S1 to step a) comprises n-butane, a stream, S10, comprising 1-butene is separated in step g) and a stream, S12, consisting essentially of 1-butene is separated from said stream S10.

6. The process of claim 1, wherein the feed stream S1 to step a) comprises n-butane and wherein 1,3-butadiene is removed from stream S6 before reacting it in step f).

7. The process of claim 1, comprising the additional steps:
   h) separating a feed stream comprising propane and n-butane into a stream, S13, comprising propane and a stream, S14, comprising n-butane;
   i) subjecting stream S14 to an isomerization reaction to provide a stream, S15, comprising n-butane and iso-butane; and
   j) combining the iso-butane of stream S15 with a part or all of stream S13 to give feed stream S1 to step a).

8. The process of claim 7, wherein n-butane is separated from stream S15 and is recycled as stream S16 to said isomerization reaction before combining the iso-butane of stream S15 with a part or all of stream S13.

9. The process of claim 1, wherein a titanium silicalite catalyst is used as epoxidation catalyst in step d).

10. An integrated process for making propene oxide and methyl tert-butyl ether comprising:
    a) a step of dehydrogenating a feed stream, S1, comprising propane and iso-butane, to provide a stream, S2, comprising propene, iso-butene and hydrogen;
    b) a separation step separating stream S2 into a stream, S3, consisting essentially of hydrogen and a stream, S4, comprising propene and iso-butene;
    c) a separation step separating stream S4 into a stream S5 comprising propene and a stream, S6, comprising iso-butene;
    d) a step of reacting a part or all of stream S5 with hydrogen peroxide in the presence of an epoxidation catalyst, providing a stream, S7, comprising propene oxide;
    e) a separation step separating propene oxide from stream S7;
    f) a step of reacting a part or all of stream S6 with methanol in the presence of a solid acid catalyst, providing a stream, S8, comprising methyl tert-butyl ether; and
    g) a separation step separating the methyl tert-butyl ether from stream S8.

11. The process of claim 10, wherein unreacted propane is separated from stream S5 and recycled as a stream, S9, to step a) before stream S5 is reacted in step d).

12. The process of claim 11, wherein a stream, S10, comprising unreacted iso-butane is separated in step g), a stream, S11, comprising more than 80% by weight iso-butane is separated from stream S10, and stream S11 is recycled to step a).

13. The process of claim 11, wherein the feed stream S1 to step a) comprises n-butane, a stream, S10, comprising 1-butene is separated in step g) and a stream, S12, consisting essentially of 1-butene, is separated from stream S10.

14. The process of claim 13, wherein 1,3-butadiene is removed from stream S6 before reacting it in step f).

15. The process of claim 11, wherein a titanium silicalite catalyst is used as epoxidation catalyst in step d).

16. An integrated process for making propene oxide and an alkyl tert-butyl ether, comprising:
    a) a step of dehydrogenating a feed stream, S1, comprising propane, n-butane and iso-butane, to provide a stream, S2, comprising propene, 1-butene, iso-butene and hydrogen;

b) a separation step separating stream S2 into a stream, S3, consisting essentially of hydrogen and a stream, S4, comprising propene, 1-butene and iso-butene;

c) a separation step separating stream S4 into a stream, S5, comprising propene and a stream, S6, comprising 1-butene and iso-butene;

d) a separation step separating unreacted propane from stream S5 and recycling it as a stream, S9 to step a);

e) a step of reacting a part or all of stream S5 from which propane has been separated in step d) with hydrogen peroxide in the presence of an epoxidation catalyst, to provide a stream, S7, comprising propene oxide;

f) a separation step separating propene oxide from stream S7;

g) a step of reacting a part or all of stream S6 with an alkanol in the presence of a solid acid catalyst, to provide a stream, S8, comprising an alkyl tert-butyl ether;

h) a separation step separating the alkyl tert-butyl ether and a stream, S10, comprising 1-butene from stream S8; and i) a separation step separating a stream S12 consisting essentially of 1-butene from stream S10.

17. The process of claim 16, wherein 1,3-butadiene is removed from stream S6 before reacting it in step g).

\* \* \* \* \*